United States Patent
Greenburg et al.

(10) Patent No.: US 6,668,836 B1
(45) Date of Patent: Dec. 30, 2003

(54) METHOD FOR TISSUE EXPANSION USING PULSATILE MOTION

(75) Inventors: Gary B. Greenburg, Millbrae, CA (US); Antony J. Fields, San Francisco, CA (US); Alexander Kazaks, Mountain View, CA (US); Joshua Korman, Los Altos Hills, CA (US)

(73) Assignee: Reconstructive Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/585,912

(22) Filed: Jun. 2, 2000

(51) Int. Cl.⁷ .................................................. A61B 19/00
(52) U.S. Cl. ........................... 128/898; 623/8; 623/915; 606/192; 600/36
(58) Field of Search .................. 623/8, 23.72, 915, 623/916; 604/175, 178, 247, 288.01, 890.1, 891.1; 128/898; 606/151, 131, 215, 217, 1, 192, 191; 600/40, 38, 39, 30, 31, 36

(56) References Cited

U.S. PATENT DOCUMENTS

| | | |
|---|---|---|
| 4,863,469 A | 9/1989 | VanBeek et al. |
| 4,955,905 A | 9/1990 | Reed |
| 5,549,640 A | 8/1996 | Fontenot |
| 5,649,960 A | 7/1997 | Pavletic |
| 5,686,303 A | * 11/1997 | Korman .................... 435/325 |
| 5,746,762 A | * 5/1998 | Bass ........................ 606/192 |
| 5,858,003 A | 1/1999 | Atala |
| 5,928,265 A | 7/1999 | Fleischmann |

FOREIGN PATENT DOCUMENTS

EP   0 279 534   8/1988

OTHER PUBLICATIONS

Wee, Sung Shin; Logan, Samuel E.; Mustoe, Thomas A. (Nov. 1992) "Continuous versus Intraoperative Expansion in the Pig Model". Plastic and Reconstructive Surgery. vol. 90, No. 5, pp. 808–814.*

Lew, Daniel; Fuseler, John W. (Feb. 1993) "The Effect of Pulsed Expansion of Subfascially Placed Expanders on the Extent and Duration of Mitosis in the Capsule and Rat Integument". Journal of Oral and Maxillofacial Surgery. vol. 51, pp. 154–158.*

* cited by examiner

*Primary Examiner*—David H. Willse
*Assistant Examiner*—Urmi Chattopadhyay
(74) *Attorney, Agent, or Firm*—Cooley Godward LLP

(57) ABSTRACT

A method of increasing the rate of expansion of tissue area and volume, either in vivo or in vitro, which comprises preparing a tissue for expansion and subjecting the tissue to stretching forces, wherein the stretching forces are alternatively increased and decreased to provide alternating periods of stretch and relax cycles.

10 Claims, No Drawings

METHOD FOR TISSUE EXPANSION USING PULSATILE MOTION

TECHNICAL FIELD

This invention resides jointly in the fields of surgery and tissue culture and is particularly directed to the expansion of animal tissue from an original, natural size to a larger size, usually with the intention of using the expanded tissue to replace defective tissue in the body of a living patient.

BACKGROUND

Tissue replacement is an essential component of reconstructive surgery after burns, trauma, tumor excision, and correction of congenital anomalies. For example, there are approximately 1 million burns per year in the U.S. alone, which result in about 100,000 admissions to burn units, about ⅓ of which require skin grafting.

The best possible skin available for grafting would be skin from the same patient taken from a donor site elsewhere on the body (referred to as an autograft). Suitable skin graft donor sites, however, are limited not only by body surface area, but can also be affected by previous graft harvest or trauma. There are times, when donor skin is limited and the amount of skin required for grafting is quite large, that sufficient autografts are not available. Because of the importance of the skin in preventing infection, either the donor skin must be used to cover a larger area than it originally covered or some suitable replacement material must be used. Harvesting of multiple skin grafts from the same donor site is often used, but such harvesting requires weeks to months between procedures for new skin to grow on the donor site. It is also a very traumatic technique, since multiple painful operations must be undertaken.

In a similar manner, other tissues also require replacement after traumatic injury, tumor excision, and other medical situations involving tissue loss. Autografts are preferred for muscle, cartilage, tendon, nerve, and other tissue replacement whenever possible in order to reduce host vs. graft immunity issues. Under appropriate circumstances, donor tissues derived from sources other than the recipient are acceptable for both skin and other tissues, but usually only as temporary replacements. For example, in patients suffering from large bums with limited donor skin sites, cadaver allografts are commonly used for temporary skin coverage, but ultimately such allografts are rejected and a permanent autograft is required. In addition, allografts also pose a risk of infection of the recipient by viruses or other disease-causing organisms present in the donor, such as infection by human immunodeficiency virus or hepatitis virus.

Artificial tissues have been developed in order to avoid the problems associated with allografts. For example, to aid in the grafting of skin on patients with limited donor areas, cultured epithelial cells derived from the patient being treated have been utilized in many grafting applications. In general, the cells are used in the form of a monolayer of epithelial cells grown on a culture medium. Preparation of such cultures requires many weeks or months, and the product is quite difficult to handle because of its fragility, even when multiple epidermal cell layers are used to form a multi-layer skin substitute.

Tissue expansion techniques, which were developed as in vivo techniques, have been used in plastic surgery for over a decade and can be helpful in increasing the area of donor tissue. Skin is not the only tissue that can be and has been expanded, although it is the most common. Other tissues have been expanded in surgical and other in vivo situations. Arteries, peripheral nerves, and skin have all been expanded in human clinical trials. Ureter, small bowel, and bladder have been expanded in animal trials.

The techniques used for in vivo tissue expansion are similar for all tissue types and involve mechanically stretching the tissue while the tissue is still attached to the patient's body. For example, by placing an expander subcutaneously and injecting it with saline, skin can be expanded and its surface area increased. This allows reconstruction with local skin after expansion of an adjacent tissue bed.

Background information in the general field of tissue expansion, including techniques suitable for skin grafting and tissue replacement, is available in the patent and scientific literature. A number of exemplary patents and scientific publications are cited below, both as examples of existing technology and to provide additional basis and support for ancillary technology related to the practice of the present invention:

U.S. Pat. No. 5,882,353 entitled "Mechanical tissue expander"
U.S. Pat. No. 5,858,003 entitled "Systems and methods for promoting tissue growth"
U.S. Pat. No. 5,855,588 entitled "Combination dissector and expander"
U.S. Pat. No. 5,788,627 entitled "Cavernosal extension implants"
U.S. Pat. No. 5,776,159 entitled "Combination dissector and expander"
U.S. Pat. No. 5,630,843 entitled "Double chamber tissue expander"
U.S. Pat. No. 5,618,310 entitled "Tissue, expansion and approximation device"
U.S. Pat. No. 5,549,713 entitled "Method for skin tissue expansion"
U.S. Pat. No. 5,507,775 entitled "Tissue expansion and approximation device"
U.S. Pat. No. 5,476,479 entitled "Handle for endoscopic surgical instruments and jaw structure"
U.S. Pat. No. 5,441,540 entitled "Method and apparatus for skin tissue expansion"
U.S. Pat. No. 5,425,760 entitled "Tissue expander apparatus, and methods of constructing and utilizing same"
U.S. Pat. No. 5,158,571 entitled "Tissue expander and method for expanding tissue"
U.S. Pat. No. 5,092,348 entitled "Textured tissue expander"
U.S. Pat. No. 5,005,591 entitled "Self-inflating tissue expander"
U.S. Pat. No. 4,904,267 entitled "Method and device for fixing a joint prosthesis"
U.S. Pat. No. 4,863,469 entitled "Method and apparatus for expanding nerve tissue"
U.S. Pat. No. 4,828,560 entitled "Spring ring tissue expander"
U.S. Pat. No. 4,800,901 entitled "Balloon-type Tissue expansion device"
U.S. Pat. No. 4,643,733 entitled "Permanent reconstruction implant and method of performing human tissue expansion"
U.S. Pat. No. 4,157,085 entitled "Surgically implantable tissue expanding device and the method of its use"
Argenta, "Controlled tissue expansion in reconstructive tissue," Brit. J. Plas. Surg., 37:520–529 (1984)
Argenta et al., "The Use of Tissue Expansion in Head and Neck Reconstruction," Ann. Plast. Surg., 11:31–37(1983).
Arons et al., "The surgical applications and implications of cultured human epidermis: A comprehensive review," Surgery, 111:4–11 (1992)

Carney, "Generation of autograft; the state of the art," Burns, 12:231–235 (1986).

Chen, "An animal experiment on short gut lengthening," Chin. Med. J. (Engl.), 110:354–357 (1997).

Gallico, "Biologic Skin Substitutes," Clinics in Plastic Surgery, 17:519–526 (1990)

Greenwald et al., "Full-Thickness Skin Wound Explants in Tissue Cultures: A Mechanical Evaluation of Healing," Plastic and Reconstructive Surgery, 90:289–294 (1992)

Kirsner et al, "The Biology of Skin Grafts," Arch. Dermatol., 129:481–483 (1993)

Liatsikos et al, "Tissue expansion: a promising trend for reconstruction in urology," J. Endourol., 14:93–96 (2000).

Nanchahal and Ward, "New grafts for old? A review of alternatives to autologous skin," Brit. J. Plas. Surg., 45:354–363 (1992)

Satar and Atala, "Progressive dilation for bladder tissue expansion," J. Urol., 162:829–831 (1999).

Stifelman and Hensle, "Ureteral tissue expansion for bladder augmentation: a long term prospective controlled trial in a porcine model," J. Urol., 160:1826–1829 (1998).

Sung Shin Wee et al., "Continuous versus intraoperational expansion in the pig model," Plastic and Reconstructive Surgery, 90:808–814 (1992)

A particularly useful advance in the field of tissue expansion was initiated by Dr. Joshua Korman, who developed the first process for in vitro skin expansion in the 1990s. The investigations of Dr. Korman resulted in the issuance of two U.S. patents, U.S. Pat. No. 5,686,303, entitled "Method of Growing Vertebrate Skin In Vitro," and U.S. Pat. No. 5,914,264, entitled "Apparatus for Growing Vertebrate Skin In Vitro." The method involves growing complete vertebrate skin in vitro by obtaining a segment of vertebrate skin, positioning the skin segment in an artificial cell-growth medium containing sufficient nutrients to maintain growth of cells of the skin, and subjecting the skin segment to stretching forces while the skin segment is in the medium. Skin produced by the method and an apparatus for carrying out the method were also disclosed in these patents.

Even this improvement, which eliminates much of the pain and discomfort associated with in vivo skin expansion, can itself be improved by increasing the rate of tissue expansion in order to improve the life of the patient who is waiting for tissue expansion to be completed so that a defective tissue can be replaced with the expanded tissue.

In the past, investigations in tissue expansion have demonstrated that use of continuous expansion forces in post operative situations over a period of three days or more is superior to intraoperative tissue expansion, even when the intraoperative procedure involved three three-minute cycles of pressure increase and decrease. See, Sung Shin Wee et al., "Continuous versus intraoperative expansion in the pig model," Plastic and Reconstructive Surgery, 90:5, 808–814 (1992). Although "cycling of pressure" is mentioned (along with other factors; p.811) in a section discussing potential additional skin expansion, there is no indication that the rate of expansion would be increased by such cycling. Instead, there is an indication that the total volume of expansion did not plateau in the study, so that a greater total volume might be obtained by use of the techniques mentioned, which include higher pressures, cycling of pressure, longer time periods, and an animal that did not lie on the expander and interrupt the expansion process.

Accordingly, it remains desirable to develop a technique that will improve the rate of tissue expansion. Investigations on rate improvement have continued in the laboratory founded by Dr. Korman, and results of those investigations are the subject of the present patent application.

SUMMARY OF THE INVENTION

Accordingly, it is an object of the invention to increase the rate of tissue expansion in all types of expansion, whether in vivo or in vitro. Although skin is the tissue most often expanded, it is an object of the invention described herein to apply the method to all types of living tissue.

It is a particular object of the invention to provide a tissue autograft having a larger volume and/or surface area than that of the donor graft site in as rapid a manner as possible.

These and other objects of the invention have been accomplished by providing a method of increasing the rate of expansion of tissue area and volume, either in vivo or in vitro. The method comprises preparing a tissue for expansion, the tissue having an initial area and volume, and subjecting the tissue to stretching forces that are alternatively increased and decreased in a controlled manner, rather than being maintained at a steady state. The increases and decreases in stretching forces are referred to as being positively modified in order to distinguish them from naturally occurring changes that may occur, for example, when movement of the body (in an in vivo expansion) causes an increase in the pressure exerted by a subcutaneous fluid expander or when stretching forces decrease naturally as tissue growth occurs (for either in vivo or in vitro expansion). Although the positively controlled increase and decrease in stretching forces can occur at any of a variety of cycle rates, manners, and durations (e.g., sinusoidal increase and decrease or rapid expansion followed by rapid force reduction), minimally there is at least one cycle per day for a period of at least one day. The expanded tissue is available for use in reconstructive surgery (or any other purpose) as soon as it has expanded to the desired size. Experimental evidence has shown that the growth in tissue size is more rapid relative to similar methods that operate without alternatively and positively increasing and decreasing the stretching forces.

In various embodiments of the invention, the stretching forces are orthogonal or radial relative to each other, but they can also be of different geometry, such as linear stretching of elongated tissues such as ligament or nerve tissue. The tissue is preferably human for use in human recipients, but veterinary use of the new skin is also encompassed by the invention. Other embodiments of the invention are set forth below in detail.

DESCRIPTION OF SPECIFIC EMBODIMENTS

The present invention combines a number of previously known techniques in a novel manner to achieve results not previously obtained. Namely, by alternatively and positively increasing and decreasing the stretching forces applied to tissue, either in vivo while the tissue is attached to a patient (or other living creature) or in vitro during tissue culture, size of the tissue can be increased more rapidly than was previously achieved using constant pressure. The reason for this increased growth rate is not known, but it is believed to be at least in part the result of providing a rest phase for tissue growth after the stress of a stretching force that realigns and/or breaks down collagen and/or other structural components of tissues. Potentially this technique could save costs by minimizing the number of surgical procedures a patient would require while also decreasing the risk associated with multiple anesthetics and surgical procedures sometimes needed in cases of complex reconstruction. Patient suffering will also be reduced, as there will be a decrease in the time that a patient must wait for tissue expansion to be completed.

There are a number of technologies ancillary to the present invention that are well developed and that thus will not be described here in great detail, such as methods for excision of the original skin or other tissue segment, production of culture media for the growth and maintenance of intact tissue when an in vitro method is used, and grafting techniques for the attachment of the graft to the host. Such methods and materials are exemplified here and references are given to scientific publications, where appropriate, so that the invention can readily be practiced. It will be recognized, however, by one of ordinary skill in the art, that many variations of these ancillary methods and materials exist and that the invention is not limited to the specific examples provided here.

In general, the method of the invention provides a method of enlarging tissue taken from a donor site of an animal donor (which includes humans). There is no limit on the tissue, other than that it is living tissue. Examples include skin, cartilage, tendon, ligament, blood vessel, nerve, and bone for use in in vitro expansions. The same tissues are preferred in in vivo applications, along with ureter and small bowel tissues. Other tissues can be expanded, but are less preferred.

Often the donor tissue is being expanded for the purpose of providing an autograft capable of covering both the original donor site, as well as a different site where tissue replacement is desired. However, the enlarged tissue is also useful for replacement of a different tissue without replacement of the original donor site (such as occurs with the harvesting of a tendon from one location of a body with the intent of replacing a different, more important tendon). Decisions on suitable donor sites are usually made by a physician and will vary, depending on the injury or disease site being repaired. Examples of donor sites and tissue collection are given in the references cited above that describe prior techniques for tissue expansion carried out prior to the present invention.

In the following description of various embodiments of the invention, the invention is described in most cases as being practiced with a human autograft. However, the invention is not so limited and can be used for both allografts (within the same species, but with the donor and recipient being different individuals) and xenografts (donor and recipient from different species). Additionally, the invention is not limited to preparation of tissue obtained from human donors, since it can be advantageously practiced to produce tissue of various vertebrates, either for veterinary use as autografts or allografts, or for use in the production of xenografts in humans (which would normally require suppression of the immune system of the human recipient when the product tissue is used as a graft). In a similar manner, artificial (but living) human or non-human tissue can be used as donor tissue for tissue enlargement. Such artificial tissues are typically those produced by genetic manipulation of natural tissues, such as by incorporation of a gene into cells of a donor tissue. Such artificial tissues are typically those produced by isolation of cells from donor tissue that are then incorporated into an artificial or modified biological substrate to create a tissue or genetic modification of a natural tissue, such as by incorporation of a gene into cells of a donor tissue.

A segment of vertebrate tissue (graft donor segment) is obtained by any of the techniques normally available for this purpose, usually surgical excision (for full-thickness skin and most other tissues) or use of a dermatome (for split-thickness skin). If a dermatome (i.e., any plane-like device for removing skin from a subject) is used, the thickness of the layer should be selected to ensure that at least some of the dermal layer is present. The tissue size will vary depending on the use for which it is intended and will vary from species to species and even from location to location on the body of an individual. For example, a typical setting for a dermatome used to prepare split-thickness human skin is about 12/1000th of an inch (about 0.3 mm).

Full-thickness skin segments for use in in vitro techniques are generally obtained by surgical excision, while split-layer skin segments for in vitro techniques are obtained by a dermatome. Both of these techniques, as well as other general techniques in the field of skin grafting, as described in Chapter 1 (pp. 1–90) of Grabb and Smith, Plastic Surgery, Little Brown & Company, Boston, Mass., USA, 4th Ed. (1991), James W. Smith and Sherrel J. Aston, eds. For tissue types other than skin intended for in vitro expansion, the donor tissue is obtained by surgical excision.

When intended for in vitro tissue expansion, the detached skin (or other tissue) is normally transferred directly to a culture medium and in most cases is not allowed to dry out before being positioned in the medium. The shape of the detached tissue segment is not material to the practice of the invention, but is often selected depending on the intended final use. Additionally, certain shapes will be better suited to individual specific apparatus variations described here. Selection and manipulation of skin or other tissue used with an in vivo expander will be made by a physician using standard techniques in the field of reconstructive surgery, as is described in the numerous references previously cited.

The size of the donor tissue is generally selected for the convenience of use, taking into consideration the intended final use, the amount of tissue available for use as donor tissue, and the apparatus that will be used to supply the stretching forces. Typical human skin segments are from 1 by 1 cm to 10 by 30 cm but can vary significantly depending on the availability of donor skin. There is generally no impact of graft size on the method of the invention, so that surgical and other procedures generally are more important in determining tissue size. For ease of handling in surgical skin grafting, segments ranging in size from 5 by 5 cm to 15 by 15 cm are preferred for in vitro uses. Similar dimensions are typical for other tissues.

Artificial cell-growth media containing sufficient nutrients to maintain growth of cells of a tissue segment are well established and need not be described here in detail for the in vitro techniques. Such media are also referred to as nutrient media or tissue-culture media. Whether any given medium will be satisfactory (if not already known) can easily be determined experimentally using the procedures for tissue growth set out in the examples below. Many such media are commercially available, such as Dulbecco's modified Eagle's medium (DMEM) with 10% added fetal calf serum. Other suitable media include basal medium (Eagle) with Hanks's BSS (85%) supplemented with calf serum (15%) and Ham's F12 medium (90%) supplemented with fetal bovine serum (10%). When serum is used to supplement an artificial medium, fetal serum is preferred, especially fetal serum from the same species as the recipient of the graft. When this is not possible or ethically desirable, the recipient's own serum can be used. For a number of media that can be used to maintain and grow tissue, see, for example, the media formulations section of any volume of the American Type Culture Collection publication entitled Catalogue of Cell Lines & Hybridomas (e.g., 5th edition, 1985, pages 265–273). This ATCC publication also contains information (in connection with specific tissue-derived cell lines) on which media are best for use with tissue or cell cultures derived from a specific tissue.

The present invention is described herein as a method. Various embodiments of an apparatus in which the method can be practiced are described below. However, a second application from the laboratory of the present inventions has been concurrently filed with the present methods application and is directed to apparatus for use with this method. The apparatus application names common inventors, is filed on the same day, is entitled "Apparatus for Tissue Expansion using Pulsatile Motion," and is identified by Ser. No. 09/585, 630. As discussed in that application (and summarized below), there are no specific limits that the method places on the apparatus, so that the method can be carried out in a variety of apparatuses (or even manually, although that is less preferred because of the obvious inconvenience of manual operation). Although various embodiments of an apparatus designed to be used with the present invention will have individual advantages, usually related to ease of use, preferred aspects of the method can be practiced with any apparatus.

The apparatus in which in vitro tissue culture and stretching takes place can vary widely, being either simple or complex. An example of a simple apparatus is a Petri (or similar) dish containing a tissue-culture medium and having a set of clamps, wires, pulleys, and weights arranged so that the clamps can be attached to a tissue segment in the medium and subjected to alternatively increased and decreased forces applied to clamps by weights attached to the clamps by the wires and suspended by the pulleys to reduce friction. The weights can then be changed on a schedule to provide the required variation in force. A more complex apparatus could contain electric motors for supplying alternating levels of force to the clamps or for circulating the culture medium in the apparatus, sensors to measure forces and stretching distances, reservoirs for fresh and waste medium, controlled atmospheres, and the like. An apparatus intended for in vitro use with the present method will comprise a container for holding a tissue culture medium, at least two connectors for holding a detached tissue segment in the culture medium, and a component that supplies opposing forces via the tissue connectors to the tissue segment (often referred to as the power subcomponent). The container can be an integral part of the apparatus or can be a separate container that is retained by the apparatus at a specific location. In the later case the connectors are "in" the container by being affixed to the apparatus that will engage the container.

An in vitro alternative apparatus can comprise a tubular fluid reservoir having an open end, a clamp located at the open end of the reservoir, where the clamp is adapted to seal the skin segment over the open end to provide a fluid-tight seal, and means for supplying hydrostatic pressure to a fluid located in the reservoir. It should be recognized here that "tubular" does not require a circular cross section, as the word is used here. Examples of means for supplying hydrostatic pressure comprises (1) a nutrient reservoir fluidly connected to the tubular fluid reservoir and being located at a higher gravitational potential than the skin segment when the apparatus is located in its normal operating position or (2) a pump fluidly connected to the tubular reservoir. A pump is any mechanical device that moves fluid from one location to another and includes a hydraulic piston. An example of a suitable clamp would be an annular member adapted to fit tightly against a flange on the open end of the tubular reservoir, with holes or grooves in the flange or annular member (or both) adapted to contain screws, bolts, wing nuts, or the like for fastening the annular member against the flange, with the skin segment being located between them to provide a fluid-tight seal at the end of the tubular reservoir with the skin being attached over the end of the reservoir as in a drum. Since freshly harvested skin is resilient (as are many other planar tissues, such as mucosal linings), no additional seal is required, but a flexible sealing member (such as an O-ring) can be provided between, e.g., the flange and annular member, if desired. Changes in the desired forces can be provided by moving the reservoir up and down relative to the tissue or by changing the pressure supplied by the pump.

In a similar manner, both simple and complex in vivo tissue expanders can be adapted to the method of the present invention. Such apparatuses typically comprise an expandable balloon-like structure that is implanted subcutaneously in the patient. Access ports are provided so that fluid can be injected into the balloon, causing it to expand and exert the stretching forces. Simple devices consist entirely of the balloon-like expander and a septum through which fluid can be manually injected through the skin via a syringe. More complex devices have percutaneous catheters leading to external pumps and pressure controllers, specific geometries intended for expansion of different tissue (or different locations of the same tissue, e.g., different skin areas), and other apparatus components.

One example of these more complex apparatuses that include pressure controllers is provided in U.S. Pat. No. 4,955,905. This patent discloses a pressure monitor for use in connection with tissue expander envelopes implanted beneath the tissue of the skin wherein a liquid is injected into the envelope to cause expansion of the skin or tissue and additional liquid is periodically injected to cause progressively increased expansion of the tissue. The tissue monitor includes means establishing direct communication between the pressure monitor and the liquid injected under pressure whereby the monitor will provide a reading of the internal liquid pressure in the envelope. The method described in this patent comprises the steps of implanting an inflatable envelope beneath the skin, injecting a sterile solution under pressure through a fill line communicating with the envelope, interrupting the flow of liquid under pressure into the envelope, sensing the pressure level of liquid injected into the envelope, and adjusting the pressure level when necessary either by removing from or injecting liquid into the envelope.

This last operation superficially resembles the method of the present invention, but differs in that there is no positive cycling of pressure, simply a monitoring of pressure, followed by an immediate adjustment if the envelope has been filled with too much liquid. This is indicated by a description in the specification that describes the events that occur in a filling sequence. After each filling sequence, the internal pressure of the envelope is read from the monitor (the internal pressure corresponds to the pressure exerted upon the surrounding tissue). If the pressure is less than desired, the filling sequence can be repeated. If the pressure is too high and thought to have the potential to cause tissue necrosis, saline solution may be removed directly from the envelope until the desired pressure is attained.

A specialized area of in vivo tissue expansion, particularly for skin, involves wound closing. Wounds that are large and open, that result from acute tissue loss, or that are infected do not lend themselves to traditional tissue expansion due to the lengthy expansion time previously required. A number of devices and techniques have emerged that are intended to take advantage of the elastic nature of skin by pulling the wound closed without irreparably damaging the skin adjacent to the open wound. These methods use attachment to the skin on opposing sides of the wound through the use of hooks, needles, sutures, or adhesives and then apply either adjustable or constant tension on the opposing wound edges to slowly close the would. Some devices require manual re-tensioning as the wound closes, while others maintain a constant tension over time through some form of automated re-tensioning. This process can take up to three days, depending on the size of the open wound. The present invention of tissue expansion using pulsatile motion can be directly applied to this specific area of tissue expansion, by applying alternating periods of stretching and relaxing as described herein, rather than the constant tensions used in the past.

A number of static wound-closure devices have been described in the prior art, including U.S. Pat. No. 5,649,960 ("Apparatus and Method for Accelerating the Stretching of Skin"), U.S. Pat. No. 5,759,193 ("Single Needle Skin Stretching Device"), U.S. Pat. No. 4,526,173 ("Skin Closure Device"), U.S. Pat. Nos. 5,486,196 and 5,893,879 (both entitled "Apparatus for the Closure of Wide Skin Defects by Stretching of Skin"), U.S. Pat. No. 5,234,462 ("Method and Kit for Accelerating the Closing of Open Skin Wounds"), U.S. Pat. No. 5,549,713 ("Method for Skin Tissue Expansion"), U.S. Pat. No. 4,825,866 ("Wound Closure Device"), and U.S. Pat. No. 5,127,412 ("Skin Tensioning"). Also see chapter 25, entitled "Alternative Devices and Techniques" in *Tissue Expansion,* Ralf E. A Nordstram, ed., Butterworth-Heinemann (1996). These devices, although used in in vivo situations, differ from balloon-like tissue expanders, in that that are attached externally to skin rather than being implanted internally in a patients body. Any of these devices can be used with the method of the present invention, either by manual operation of the devices so as to provide a series of cycles that add and remove tension on the skin or by modifying the devices so that such cycles are produced automatically.

A key aspect of the present invention is subjecting a tissue to stretching forces that are positively controlled so that the tissue experiences a "stretch and relax" cycle. Here "stretching forces" means a force or forces applied to the tissue in one or more direction in which expansion (i.e., tissue growth) is desired. Because of the physical nature of stretching forces, at least two opposed forces are applied to a tissue (because of Newton's familiar law of equal and opposite forces). If only two opposed forces are present the stretching is along a line coaxial with the stretching forces, subject to some additional stretching along adjacent regions of the tissue. This is the simplest stretching situation, but is not particularly desired (other than for substantially linear tissues, such as nerve, tendon, and ligament tissue) because of the resulting tissue deformation. Additional forces can be applied to provide for more regular stretching of volumetric or planar tissues, such as muscle or skin. Parallel opposed forces (such as would be applied by two broad, rigid clamps attached to opposite ends of a detached skin segment) lead to stretching along a single dimension of a tissue. Non-parallel multiple stretching forces (e.g., radial outward from a central point or orthogonally in the plane of a tissue) result in stretching in both of the two dimensions of a planar tissue (e.g., the two dimensions parallel to the plane of a skin surface). Forces can be supplied in three dimensions as well.

Forces can be applied to planar tissues, such as skin, that are not entirely parallel to the skin surface. However, some portion of the force must be parallel to the planar surface for stretching to take place. For example, when used with in vitro stretching of skin, a convex solid surface or a fluid forced against the face of a detached skin segment whose edges are fixed will cause the skin segment to be subjected to forces both orthogonal and parallel to the surface of the skin; such stretching comes within the scope of the present invention. This is the type of stretching of skin that occurs with the fluid-expandable balloons and envelopes that are common in in vivo skin expansion.

When a detached tissue segment is being stretched in an in vitro application, the ends of the segment are held in place in the tissue culture by some physical apparatus. Any apparatus that can be used to hold the ends in place can be used. An attachment apparatus is needed for each point to which a force will be applied. Typical attachment apparatuses include clamps, hooks, sutures, and glue. A clamp can be narrow (e.g., less than ¹⁄₁₀ the length of the edge being held) or broad (up to or greater than the width of the edge, and generally considered broad when greater in width than ½ the width of the edge of the tissue being clamped). If opposed broad clamps are used, stretching between the ends of the clamp will generally be restricted if an orthogonal stretching force is also present on the skin. For maximum stretching efficiency, multiple attachment points capable of moving away from each other during the stretching process are preferred. For example, multiple small hooks or clamps attached in a generally circular manner to a circular detached skin segment and subjected to forces applied radially outward from the center of the segment automatically move away from each other as stretching proceeds, thus supplying stretching forces along the tangents of the circle as well as along its radii.

The forces themselves can be supplied by any means for supplying force, such as a weight, spring, or motor. The force being applied at any given point of the cycle can be either static or dynamic. Here a static force is one that is applied between two attachment points that do not move further apart from each other as cell growth and division occurs. Such growth reduces over time the force between the attachment points. For example, two clamps can be attached to opposite ends of a detached skin segment, with one (or both) of the clamps being attached to a screw that the distance between the clamps can be varied. Turning the screw to move the clamped ends away from each other produces an initial force on the skin segment, but this force decreases as cells in the skin grow and divide. A dynamic force, on the other hand, is one provided between two attachment points that are capable of relative movement so that a constant force can be maintained. For example, two clamps can be attached to weights that are suspended via a pulley system from opposite ends of a detached skin segment. The force on the skin segment in such an apparatus remains constant as the skin grows and divides.

The amount of force applied at any given point in time to a tissue during a stretch phase is minimally that required to cause the tissue to stretch and will not exceed the amount that causes the tissue to rupture. Since the strength of different tissues obtained vary (even tissues obtained from different locations of the same donor/recipient of an autograft), the forces are best determined empirically. Minimum stretch-cycle force is that which causes some stretch to take place. Maximum stretch-cycle force is that which causes tissue necrosis. Preferably, maximum force is less (typically at least 5% less) than that which causes blanching of tissue as a result of the inability of the tissue to maintain blood flow through internal blood vessels. In in vivo situations, patient pain will also be significant in determining maximum forces that can be used.

For example, with the use of human skin, stretching of at least 2% per day is desired, preferably at least 5%, more preferably at least 10%. Non-human skin can be either tougher or less tough (here "tough" refers to resistance to stretching) than human skin and thus may be stretched correspondingly less or more than these amounts. In general skin can be stretched until rupture or cell death induced by the tension of stretching, which can readily be followed by histological examination. In some cases it may be desirable to keep stretching under 15% per day to avoid cell death, in other cases under 12%. However, the maximum sustainable stretch rate is best determined empirically, using these numbers as initial guidelines. When skin is initially placed in the nutrient medium, it should be stretched back to original in vivo size before actual stretching is measured, since skin removed from a body generally shrinks to less than its original dimensions.

In many cases, the actual forces will never be measured or known, such as in a screw-based apparatus. However, typical forces for skin range from zero to 300 g per attachment point, preferable zero to 150 g per attachment point, using one attachment point per cm of skin perimeter. As there is variation from patient to patient in strength of skin and other tissues, one should start with a force at the lower end of the range and increase forces gradually during the initial stretch, paying attention to counter indications, such as cracking or tearing of the tissue. Instead of calculating on a per attachment basis, force can be measured per unit area. This is particularly useful for skin, as area of coverage is often the matter of primary interest. For example, skin in the form of a disk 2.93 cm in diameter, having an area of 6.75 $cm^2$, preferably has an applied force of 75–225 $g/cm^2$, more preferably 150 $g/cm^2$. On a per attachment scale, this translates to a range of 50–200 g/attachment, preferably 100 g/attachment.

Positive control of the stretch and relax cycles is an important part of the present invention. The "stretch" phase of a cycle occurs while stretching forces are increasing or are being maintained at a level that causes stretching to occur. The "relax" phase of the cycle occurs when stretching forces are decreasing or are being maintained at a level less than the maximum used during the preceding "stretch" phase. Stretching forces on the tissue can fall to zero during the relax phase, but also can be maintained at a fraction of the force applied during the stretch phase, such as one-half, one-third, or one-quarter of the maximum stretch force.

Because a goal of the present invention is to maximize the rate of tissue expansion, the stretch phase will typically apply the maximum stretching forces that can be sustained without harm to the tissue for the stretch period being used. Relatively higher forces have been found to be acceptable for tissue when applied for shorter periods, while longer stretch cycles are expected to have better success when less than the maximum stretching force is applied.

Forces during the relax phase may not be zero but can be maintained at some positive value in order to maintain some minimal stretching force on the tissue as it recovers from the stretch phase. Typically, the relax phase will have a minimum force that falls in the range of from zero to 0.9 (preferably zero to 0.5, more preferably zero to 0.3, even more preferably zero to 0.1) times that of the maximum stretch-phase force. Most preferably the relax phase minimum will occur with no force being applied to the tissue being expanded.

In order for the present invention to be practiced, stretch and relax periods must alternate. The precise manner in which they alternate, however, is less important. For example, an automated apparatus (used either in vivo or in vitro) can cycle through a series of stretch and relax periods in a simple "on/off" mode (i.e., a graph of pressure versus time would appear as a square wave). Force can also increase (and later decrease) through a series of steps separated by periods of constant force, rather than through a single increase in force. On the other hand, use of two expandable reservoirs, with fluid being pumped back and forth between the two, would produce a sinusoidal graph of stretching forces at the two locations (with each location being out of phase relative to the other; i.e., one location would be in a rest phase while the other is in a stretch phase). Other techniques (such as raising and lowering of a fluid reservoir connected to a single expander) will also produces sinusoidal force/time effects.

Successive cycles can have the same maximum and minimum pressures if desired, although this is not required. Because tissue expansion occurs slowly over time, a typical pattern of pressure cycles will result in slightly lower pressures being exerted with each cycle as stretching occurs and relieves the pressure, unless the expander is adjusted for the new resistance of the skin or other tissue being expanded. For example, in the on/off and two-reservoir systems just mentioned, each cycle will produce slightly lower pressure at the expansion sites unless additional fluid is added to the system (or greater motion of a stretching arm occurs) to make up for the volume added from tissue expansion. However, one can use dynamic forces or can use force applicators (e.g., motors) with feedback control in order to provide the same force (or a pattern of increase and/or decrease in maximum and/or minimum force) in successive cycles, if desired.

The time period of one stretch/relax cycle can vary considerably. One cycle per day (approximately) is the minimum needed to see an increase in expansion rate relative to static application of stretching forces or relative to use of an initial static stretching force or pressure followed by a slow decrease in forces as tissue expansion occurs. Rapid cycling is also possible and appears to improve the expansion rate, perhaps because of an improvement in the circulation of blood or other nutrients through tissue. There is no specific maximum cycle rate, but approximately 100 times per minute is a useful practical limit for many tissues in order to avoid the dangers associated with rapid movement and the possibility of tissue tears or ruptures. More typical cycle rates are from 1 cycle per 10 minutes to 50 cycles per minute, preferably from 1 to 25 cycles per minute, and more preferably from 5 to 15 cycles per minute.

It is not necessary that the stretch and relax phases have the same length, nor need they occur continuously. For example, a series of relatively rapid stretch and relax cycles (an "active" stage) can be followed by a relatively long relax phase (an "off" stage) to allow tissue recovery and growth. A typical example of this technique (illustrated with an operating cycle frequency of 10 stretch and relax cycles per minute) would have an active stage lasting 18 seconds (3 cycles) followed by an off stage lasting 42 seconds (7 "cycles").

The duration of the tissue expansion process will vary with the health and condition of the donor tissue, the extent of expansion necessary for the particular donor tissue being expanded, the health of the patient/recipient of the tissue, and on many other medical factors that are outside the scope of this invention. One day (24 hours) can be considered to be the lower limit of the time during which tissue expansion with pulsatile motion is likely to be practiced, from a practical point of view. Shorter periods of time do not provide sufficient expansion to require the greater complexity of the invention, relative to standard techniques of tissue expansion. There is also no limit on maximum duration, other than patient discomfort in in vivo situations and tissue viability during tissue culture. The advantages of the method of the invention relative to non-pulsatile techniques will be more apparent as the duration of treatment increases, so that minimum expansions of two days or more are preferred.

These examples of cycles, including factors such as force/time relationships, relative forces, duration of the process, and the like, should not be considered to be limiting, as many other force/time waveforms will give satisfactory results of increased expansion rate relative to that which is obtained in the absence of alternating stretch/relax cycles.

A typical expanded tissue has an area or volume after being subjected to stretching forces (over an appropriate length of time) that is at least twice that of the tissue prior to being subjected to the stretching forces. The stretched tissue can be used as a graft or (in in vitro situations) can be divided into further segments so that one or more of the further segments is subjected again to the method of the invention. As long as cell growth continues, new normal tissue can be produced from parts of the original donor graft. For example, skin having a surface area at least two times that of the original donated skin segment can be provided in one stretching operation (which may last over several days), usually at least four times, and often at least eight that of the original. Since the stretched tissue can be divided and the resulting segments re-stretched, exponential production of skin and other tissue is possible, particularly in in vitro situations.

Once a stretched tissue graft product has been prepared, it is used in grafting in the same manner as an unstretched graft donor tissue.

The invention now being generally described, the same will be better understood by reference to the following detailed examples of the invention, which are provided here for illustration only and are not to be considered limiting of the invention unless so specified.

EXAMPLE

Human full thickness skin was obtained from discarded surgical material following abdominoplasty under informed consent. Immediately upon removal the tissue was placed in 2 liters of sterile transport media, epidermal side up and transported to the laboratory at 4° C. The tissue was defatted using standard aseptic technique, and 6.74 cm$^2$ punches were made using a hardened steel blade. The circular tissue was placed epidermal side up in the expansion device described in the detailed description above and was attached to the device using nylon "T" tags that were inserted through the tissue in a radial pattern of equal spacing. Medium was added, and initial tension was set to 100 g per attachment. The device was sealed and the motor activated to begin force cycling at 10 cycles per minute. The tissue area was measured prior to initiating cycling. Control tissue was placed in an organ culture device in which the tissue sits on a stainless steel grid (under no load) or was set up in an expansion device as described under tension but was not cycled. The tissue was incubated at 37° C. The media was composed of DMEM containing 4.5 g/L glucose and the following additives: L-glutamine, 2 mM; hydrocortisone, 0.28 $\mu$M; insulin, 4.4 $\mu$M; ascorbic acid, 0.3 mM; penicillin, 105 U/L; streptomycin, 100 mg/L. The device was operated in an air atmosphere with $CO_2$ added for buffering capacity and $O_2$ to prevent hypoxia, as necessary.

After stretching, the skin was measured and removed from the device. The tissue was then prepared for histology, biochemical analysis, and animal transplantation. Tissue appeared to be viable under histological examination and other forms of examination after stretching.

After five days in culture full thickness human skin that had been stretched by applying a cycling load increased 3 fold in surface area. The tissue remained viable with an intact epidermis and dermis. When skin from the same patient was either placed under no load or placed under 100 g/attachment of load but not cycling, there was no significant increase in surface area that could be measured during the same time period. This example illustrates that pulsatile tissue expansion not only allowed rapid tissue expansion, but also allowed tissue expansion to occur at a force less than that necessary to cause expansion in the absence of pulsatile motion.

| | % Increase in Surface Area | | | | | |
|---|---|---|---|---|---|---|
| Day | 0 | 1 | 2 | 3 | 4 | 5 |
| No Load | 0 | 0 | 0 | 0 | — | — |
| Static Load | 0 | 3 | 1 | 0 | 0 | 0 |
| Cyclical Load | 0 | 21 | 53 | 120 | 151 | 203 |

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What we claim is:

1. A method of increasing the rate of expansion of tissue area and volume for a given expansion force in a post-operative in vivo tissue expansion process after a balloon tissue expander has been surgically and operably inserted adjacent to a previously intact tissue, which comprises:
    subjecting said tissue to stretching forces that alternatively increase and decrease over multiple cycles during a period of tissue expansion, wherein said method comprises at least one cycle per day for a period of at least one day.

2. The method of claim 1, wherein said stretching forces are reduced during a relax phase to less than 0.9 times the maximum stretching force applied during a stretch phase.

3. The method of claim 2, wherein the relax phase has a minimum stretching force of zero.

4. The method of claim 1, wherein said intact tissue is a skin or mucosal segment.

5. The method of claim 4, wherein intact tissue is a skin segment and said skin segment is human skin.

6. The method of claim 1, wherein said tissue is an elongated tissue selected from the group consisting of tendon, ligament, blood vessel, nerve, ureter, and bowel tissue.

7. The method of claim 6, wherein said stretching forces stretch said tissue primarily in one dimension.

8. The method of claim 1, wherein said method provides a cycle period in a range from 1 cycle per 10 minutes to 50 cycles per minute.

9. The method of claim 8, wherein said cycle period is in a range from 1 cycle per minute to 25 cycles per minute.

10. The method of claim 8, wherein said cycle period is in a range from 5 cycles per minute to 25 cycles per minute.

* * * * *